(12) United States Patent
Sarac et al.

(10) Patent No.: US 8,020,275 B2
(45) Date of Patent: Sep. 20, 2011

(54) METHOD FOR COMPRESSING INTRALUMINAL PROSTHESES

(75) Inventors: Timur P. Sarac, Chagrin Falls, OH (US); Rajesh Khosla, Beachwood, OH (US)

(73) Assignees: The Cleveland Clinic Foundation, Cleveland, OH (US); Peritec Biosciences, Ltd., Cleveland, OH (US)

( * ) Notice: Subject to any disclaimer, the term of this patent is extended or adjusted under 35 U.S.C. 154(b) by 1284 days.

(21) Appl. No.: 11/601,074

(22) Filed: Nov. 16, 2006

(65) Prior Publication Data

US 2007/0199360 A1    Aug. 30, 2007

Related U.S. Application Data

(60) Provisional application No. 60/738,107, filed on Nov. 17, 2005.

(51) Int. Cl.
    *B23P 19/04*    (2006.01)
(52) U.S. Cl. ........ 29/460; 29/527.2; 623/1.22; 623/1.42
(58) Field of Classification Search .................... 29/460, 29/527.2, 527.4, 592.1, 729, 739; 623/1.42, 623/1.12, 1.22; 606/1, 108, 194–200
    See application file for complete search history.

(56) References Cited

U.S. PATENT DOCUMENTS

| | | |
|---|---|---|
| 4,553,545 A | 11/1985 | Maass et al. |
| 4,776,337 A | 10/1988 | Palmaz |
| 5,376,110 A | 12/1994 | Tu et al. |
| 5,534,007 A | 7/1996 | St. Germain et al. |
| 5,571,166 A | 11/1996 | Dinh et al. |
| 5,591,223 A * | 1/1997 | Lock et al. .................... 623/1.17 |
| 5,746,764 A | 5/1998 | Green et al. |
| 5,746,766 A | 5/1998 | Edoga |
| 5,810,838 A | 9/1998 | Solar |
| 5,860,966 A | 1/1999 | Tower |
| 5,911,752 A | 6/1999 | Dustrude et al. |
| 5,922,393 A | 7/1999 | Jayaraman |
| 5,944,735 A | 8/1999 | Green et al. |
| 5,971,992 A | 10/1999 | Solar |
| 5,972,028 A | 10/1999 | Rabenau et al. |
| 6,009,614 A | 1/2000 | Morales |
| 6,045,568 A | 4/2000 | Igaki et al. |
| 6,063,092 A | 5/2000 | Shin |

(Continued)

FOREIGN PATENT DOCUMENTS

EP    0 948 946 A1    10/1999

(Continued)

OTHER PUBLICATIONS

Copending U.S. Sarac et al. Patent Application filed Nov. 16, 2006 entitled "Apparatus and Method for Delivering Lined Intraluminal Prostheses".

*Primary Examiner* — Minh Trinh

(74) *Attorney, Agent, or Firm* — Tarolli, Sundheim, Covell & Tummino LLP

(57) ABSTRACT

A method for compressing an intraluminal prosthesis provides a mesh tube having first and second longitudinally spaced tube ends and a hollow tube bore located therebetween. The intraluminal prosthesis is completely inserted into the hollow tube bore. The tube is stretched in a longitudinal dimension, which reduces the tube in a radial dimension and causes the intraluminal prosthesis to radially compress.

3 Claims, 3 Drawing Sheets

U.S. PATENT DOCUMENTS

| | | | |
|---|---|---|---|
| 6,080,190 A * | 6/2000 | Schwartz | 623/1.22 |
| 6,183,503 B1 | 2/2001 | Hart et al. | |
| 6,249,952 B1 | 6/2001 | Ding | |
| 6,295,714 B1 | 10/2001 | Roychowdhury et al. | |
| 6,352,547 B1 | 3/2002 | Brown et al. | |
| 6,387,117 B1 | 5/2002 | Arnold, Jr. et al. | |
| 6,416,544 B2 | 7/2002 | Sugita et al. | |
| 6,432,134 B1 * | 8/2002 | Anson et al. | 623/1.19 |
| 6,582,472 B2 | 6/2003 | Hart | |
| 6,685,735 B1 | 2/2004 | Ahari | |
| 6,745,445 B2 | 6/2004 | Spilka | |
| 6,755,855 B2 | 6/2004 | Yurek et al. | |
| 6,790,221 B2 | 9/2004 | Monroe et al. | |
| 6,821,291 B2 | 11/2004 | Neisz et al. | |
| 6,860,898 B2 | 3/2005 | Stack et al. | |
| 6,878,158 B2 | 4/2005 | Shin et al. | |
| 6,915,560 B2 | 7/2005 | Austin | |
| 6,939,361 B1 * | 9/2005 | Kleshinski | 606/200 |
| 2004/0181236 A1 | 9/2004 | Eidenschink et al. | |
| 2005/0033404 A1 | 2/2005 | Eidenschink | |
| 2005/0165352 A1 | 7/2005 | Henry et al. | |
| 2005/0267562 A1 | 12/2005 | Jones et al. | |

FOREIGN PATENT DOCUMENTS

| | | |
|---|---|---|
| EP | 0 970 711 A2 | 1/2000 |
| EP | 0 970 711 A3 | 1/2001 |
| EP | 1 095 634 A2 | 5/2001 |
| EP | 1 226 798 A2 | 7/2001 |
| EP | 0 970 711 B1 | 10/2004 |
| WO | WO 96/00099 | 1/1996 |
| WO | WO 99/33410 A2 | 7/1999 |
| WO | WO 99/33410 A3 | 7/1999 |

* cited by examiner

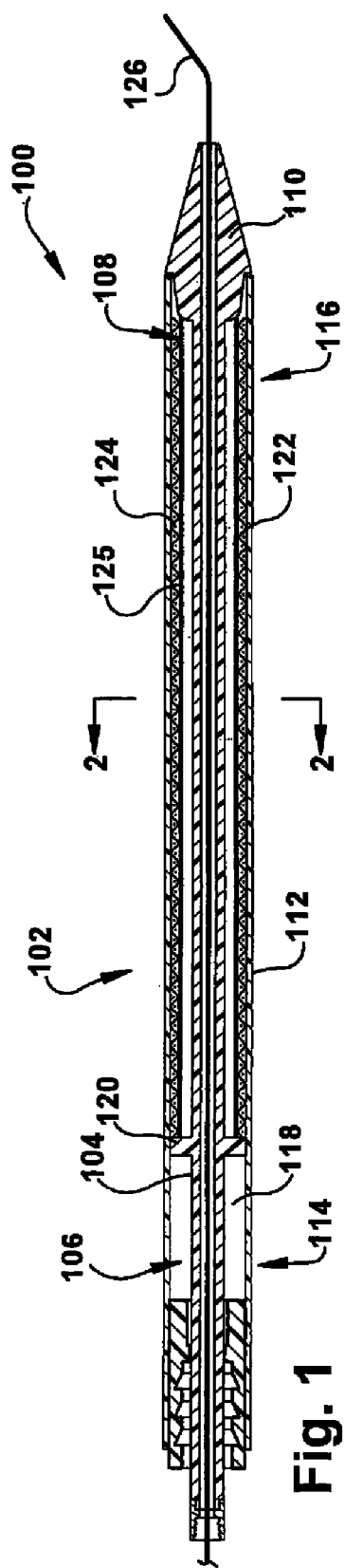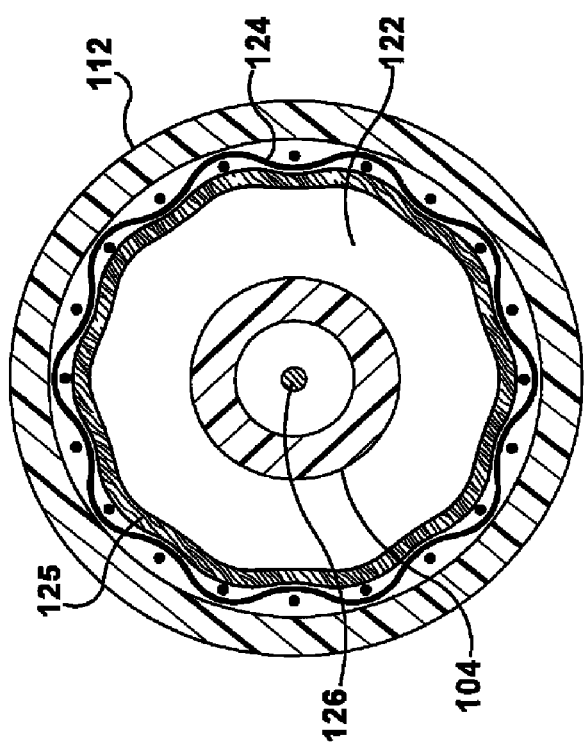

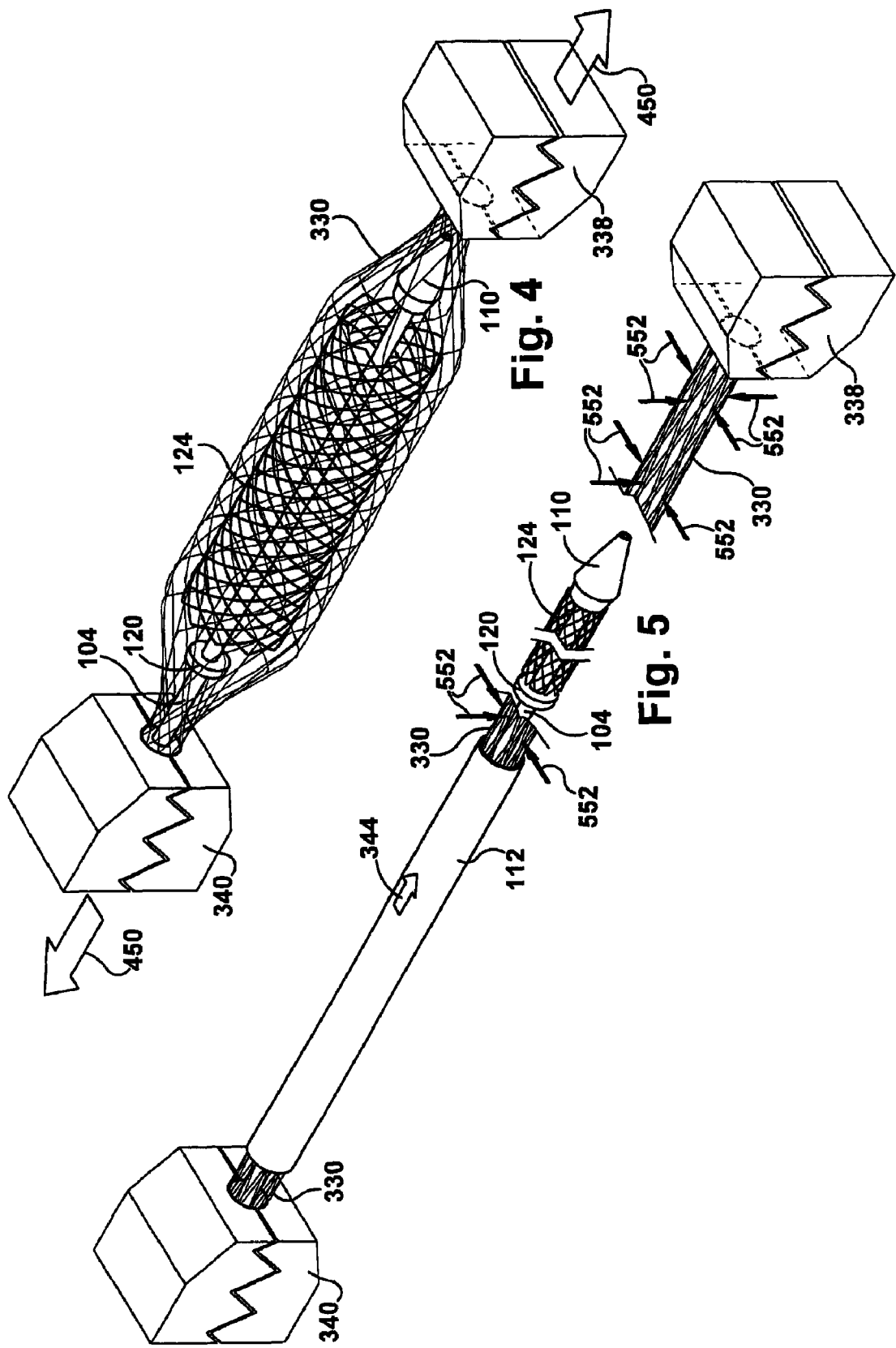

METHOD FOR COMPRESSING INTRALUMINAL PROSTHESES

RELATED APPLICATION

This application claims priority from U.S. Provisional Patent Application Ser. No. 60/738,107, filed Nov. 17, 2005, the subject matter of which is incorporated herein by reference.

TECHNICAL FIELD

The present invention relates to an apparatus and method for use of compressing intraluminal prostheses and, more particularly, to compressing lined intraluminal prostheses for storage or installation using an intraluminal prosthesis cartridge.

BACKGROUND OF THE INVENTION

A common method of treatment used in restoring blood flow through a diseased segment of a blood vessel is balloon angioplasty. This treatment generally involves the use of a balloon catheter. The balloon catheter is introduced into the cardiovascular system of a patient through an artery, such as the brachial or femoral artery, and is advanced through the vasculature until the balloon attached to the distal end of the catheter reaches the diseased vessel. The balloon is placed across the diseased vessel segment and is inflated with sufficient pressure to cause the deposit on the intravascular surface to compress against the vessel wall. The balloon is then deflated to a small profile so that the balloon catheter may be withdrawn from the patient's vasculature and the blood flow resumes through the dilated artery.

Angioplasty of an artery to correct flow obstruction in the vessel may stimulate excess tissue proliferation which then blocks (through restenosis) the newly reopened vessel, precipitating a need to perform a second angioplasty procedure. Alternatively, a more drastic procedure such as a surgical bypass operation may be required to repair or strengthen the vessel. To reduce the likelihood of restenosis and to strengthen the diseased vessel segment, an intravascular intraluminal prosthesis may be implanted within the segment of the diseased vessel to maintain vascular patency.

Intraluminal prostheses are tubular structures, such as a stent, graft, patch, or the like, which are radially expandable to hold a narrowed blood vessel in an open configuration. While intraluminal prostheses are most often used to hold blood vessels open, intraluminal prostheses can also be used to reinforce collapsed or narrowed tubular structures in the respiratory system, the reproductive system, biliary ducts or any other tubular body structure. The intraluminal prosthesis is typically transported through the patient's vasculature in a small, compressed delivery configuration, and then is enlarged to a larger, expanded configuration at the implantation site. The expansion is often accomplished by inflation of a balloon portion of the catheter contained within the compressed intraluminal prosthesis, but self-expanding intraluminal prostheses made from a memory alloy or spring-like structure may be used, with or without a balloon assist.

Since the catheter and intraluminal prosthesis will be traveling through the patient's vasculature, the intraluminal prosthesis must be compressed to a small delivery diameter and must be firmly attached to the catheter before insertion into the body. Thus, the intraluminal prosthesis must be positioned on the catheter so as not to interfere with delivery, and the intraluminal prosthesis must not slip off the catheter before it reaches the desired location for deployment.

In conventional procedures, it is necessary to crimp the intraluminal prosthesis onto the catheter, optionally with a balloon inside the intraluminal prosthesis, to reduce the intraluminal prosthesis's diameter and to prevent it from sliding off the catheter while the catheter is advanced through a patient's vasculature. Non-uniform crimping can result in relatively sharp edges being formed along the uneven surface of the compressed intraluminal prosthesis. In addition, non-uniform intraluminal prosthesis compression may result in an intraluminal prosthesis/catheter profile that is larger than necessary. Where the intraluminal prosthesis is not reliably compressed onto the catheter, the intraluminal prosthesis may slide off the catheter and into the patient's vasculature prematurely, which may cause thrombosis. Thus, it is important to ensure the proper compression of an intraluminal prosthesis onto a catheter in a uniform and reliable manner.

Manual crimping of the intraluminal prosthesis tends to result in uneven compression due to uneven application of force. Furthermore, it is difficult to determine when a uniform and reliable compression has been achieved by hand. In addition, due to the flexible nature of the intraluminal prosthesis, some self-expanding intraluminal prostheses are difficult to load by hand into a balloon catheter. Minimizing direct human manipulation may decrease the likelihood of human error, and increase the consistency of the compression procedure. Hence, there is a need for a device for reliably and uniformly compressing an intraluminal prosthesis onto a catheter.

There are several known mechanisms devised for loading an intraluminal prosthesis onto a catheter. For example, U.S. Pat. No. 5,911,452 shows a chamber with a flexible tubular diaphragm into which a deflated balloon catheter can be inserted with the intraluminal prosthesis. The chamber is then pressurized to crimp the intraluminal prosthesis onto the deflated catheter balloon. U.S. Pat. No. 6,009,614 shows another intraluminal prosthesis crimping chamber utilizing fluid pressure to crimp the intraluminal prosthesis onto a deflated catheter balloon. U.S. Pat. No. 5,810,838 shows further examples of pressurized chambers and collapsible tubular sleeves for compressing intraluminal prostheses onto balloon catheters. U.S. Pat. No. 5,971,992 shows yet another example of a pressurized chamber. U.S. Pat. No. 5,746,764 shows further devices for compressing intraluminal prosthesis onto balloon catheters that include both vacuum and pressurizing fluid pressure means for compression of the intraluminal prosthesis onto the catheter balloon. U.S. Pat. No. 5,944,735 shows yet another example of the intraluminal prosthesis compression device. U.S. Pat. No. 5,972,028 shows another variation of an intraluminal prosthesis compression device. U.S. Pat. No. 5,860,966 shows another version of an intraluminal prosthesis compression apparatus employing a pressurized diaphragm to compress the intraluminal prosthesis. Finally, U.S. Pat. No. 6,745,445 shows inflating an angioplasty balloon inside a vascular intraluminal prosthesis in order to secure the vascular intraluminal prosthesis upon the balloon and applying uniform compression pressure around the balloon/intraluminal prosthesis unit. The pressure chambers of these various patents require time-consuming and expensive calibration and maintenance in order to assure uniform and complete compression of the intraluminal prostheses. A method that enhances uniform distribution of the compression pressure and/or reduces the necessary calibration and maintenance would allow more even distribution of pressure during the intraluminal prosthesis compression process.

In addition, it is desirable to hold the intraluminal prosthesis in a compressed position inside the catheter for installation in the patient and possibly for an extended storage period. Particularly in the case of a self-expanding intraluminal prosthesis, it may be difficult for a user to prevent a compressed intraluminal prosthesis from expanding upon removal from one of the above pressure chambers.

Lined intraluminal prostheses, which have a layer of synthetic or biological material covering at least part of an inner or outer surface of the intraluminal prosthesis, are becoming more prevalent as technologies arise to facilitate provision and use of such lined intraluminal prostheses in an economical and efficient manner. These lined intraluminal prostheses present particular challenges to achieving compression and storage as desired. Lined intraluminal prostheses have an increased wall thickness as compared to unlined intraluminal prostheses, and this extra bulk may necessitate higher pressure to compress the lined intraluminal prosthesis than might be required by an unlined intraluminal prosthesis. Care must also be taken that structures of the intraluminal prosthesis do not wear away or puncture the relatively delicate lining during the compression process, particularly under the increased compression forces needed for the lined intraluminal prosthesis. Additional considerations arise when the lining is biological, as natural tissue linings must be kept hydrated to avoid cracking and breakage.

Accordingly, it is desirable to provide a method and apparatus of compressing intraluminal prostheses which economically and efficiently provides even compression pressure, allows for ease in transporting and storing a compressed intraluminal prosthesis, and avoids mechanical or dehydration damage to a lined intraluminal prosthesis.

SUMMARY OF THE INVENTION

In an embodiment of the present invention, a method for compressing an intraluminal prosthesis is described. A mesh tube is provided, the mesh tube having first and second longitudinally spaced tube ends and a hollow tube bore located therebetween. The intraluminal prosthesis is completely inserted into the hollow tube bore. The tube is stretched in a longitudinal dimension, which reduces the tube in a radial dimension and causes the intraluminal prosthesis to radially compress.

In an embodiment of the present invention, a method for compressing an intraluminal prosthesis to an airless state is described. The intraluminal prosthesis is submerged in a liquid bath before compression. Air is expressed from the intraluminal prosthesis. The intraluminal prosthesis is compressed to a reduced diameter condition. The intraluminal prosthesis is removed from the liquid bath after compression.

In an embodiment of the present invention, an apparatus for compressing an intraluminal prosthesis is described. A mesh tube has longitudinally separated first and second tube ends and a hollow tube bore adapted to receive the intraluminal prosthesis. A first attachment block is removably attached to the first tube end. A second attachment block is removably attached to the second tube end. A block frame connects the first and second attachment blocks for relative longitudinal motion therebetween. The block frame moves at least one of the first and second attachment blocks. The relative movement between the first and second blocks stretches the tube longitudinally, which causes the tube to constrict radially and thereby radially compress the intraluminal prosthesis.

In an embodiment of the present invention, an apparatus for compressing an intraluminal prosthesis to an airless state is described. The apparatus includes a liquid bath and a compression structure. The compression structure is at least partially submerged within the liquid bath, and is adapted to both express air from the intraluminal prosthesis and radially compress the intraluminal prosthesis while the intraluminal prosthesis is submerged within the liquid bath.

BRIEF DESCRIPTION OF THE DRAWINGS

For a better understanding of the invention, reference may be made to the accompanying drawings, in which:

FIG. 1 is a partial side view of an intraluminal prosthesis cartridge produced using one embodiment of the present invention;

FIG. 2 is a cross-sectional view taken along line 2-2 of FIG. 1;

FIG. 4 is a partial perspective view of one embodiment of the present invention in a first condition; and FIG. 5 is a partial perspective view of the embodiment of FIG. 4 in a second condition.

DESCRIPTION OF EMBODIMENTS

Figure 3:
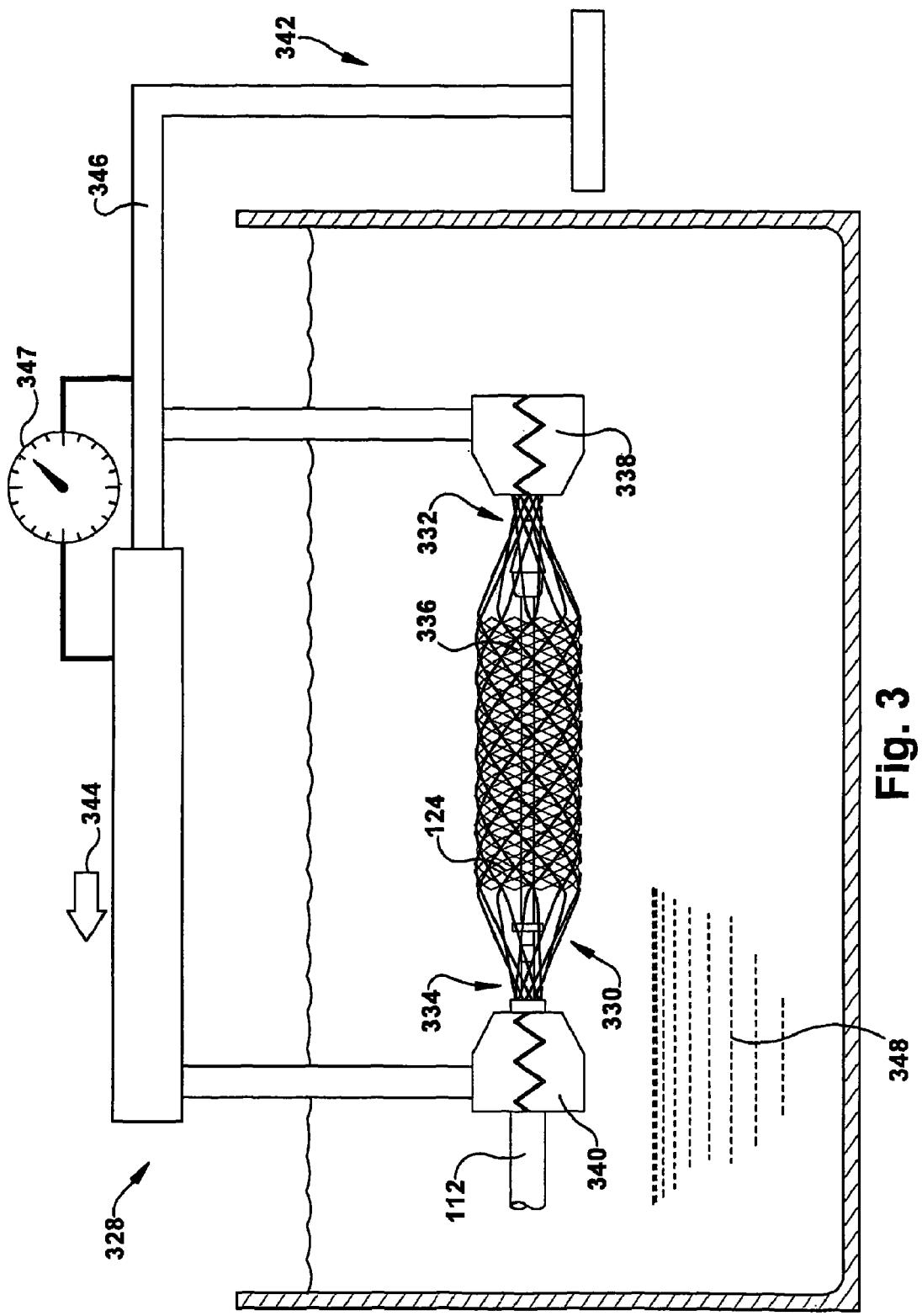
FIG. 3 is a side view of an embodiment of the present invention.

In accordance with the present invention, FIG. 1 depicts an intraluminal prosthesis cartridge 100 adapted for operative connection to a delivery catheter 102. The intraluminal prosthesis cartridge 100 and the delivery catheter 102 are described in greater detail in copending U.S. Sarac et al. patent application entitled "Apparatus and Method for Delivering Lined Intraluminal Prostheses", which claims priority from U.S. Provisional Application No. 60/738,107, both of which are hereby incorporated by reference in their entirety.

The intraluminal prosthesis cartridge 100 includes a cartridge inner sheath 104 having longitudinally spaced proximal and distal cartridge inner sheath ends 106 and 108, respectively. A nose cone 110 is connectable to the distal cartridge inner sheath end 108. An intraluminal prosthesis sheath 112 has longitudinally spaced proximal and distal intraluminal prosthesis sheath ends 114 and 116, respectively. A hollow intraluminal prosthesis sheath bore 118 at least partially surrounds the cartridge inner sheath 104. The intraluminal prosthesis sheath 112 is adapted for longitudinal movement relative to the cartridge inner sheath 104. A stopper 120 is connectable to the cartridge inner sheath 104 at a location longitudinally spaced from the nose cone 110. The stopper 120 extends radially between the cartridge inner sheath 104 and the intraluminal prosthesis sheath 112.

An annular intraluminal prosthesis space 122 is defined radially between the intraluminal prosthesis sheath 112 and the cartridge inner sheath 104 and longitudinally between the stopper 120 and the nose cone 110. The annular intraluminal prosthesis space is adapted to contain a compressed intraluminal prosthesis 124, as shown in FIG. 2. The intraluminal prosthesis 124 of FIGS. 1 and 2 is depicted as being a lined intraluminal prosthesis, having a layer of synthetic or biological material covering at least part of an inner or outer surface of the intraluminal prosthesis. The layer is shown here as an inner lining 125. The inner lining 125 is omitted from subsequent Figures for clarity. A lined or unlined intraluminal prosthesis 124 may be chosen for use with the present invention as desired for a particular application.

It is contemplated that a guidewire 126 may extend through a center portion of the intraluminal prosthesis cartridge 100. The guidewire 126 may provide assistance in attaching the intraluminal prosthesis cartridge 100 to the delivery catheter 102. The guidewire 126 may also or instead assist in guiding the intraluminal prosthesis cartridge 100 to a desired deployment site, such as by using the Seldinger technique.

The apparatus 328 shown in FIG. 3 may be used to compress an intraluminal prosthesis 124 in a uniform and symmetrical manner. The apparatus 328 includes a mesh tube 330 having longitudinally separated first and second tube ends 332 and 334, respectively, and a hollow tube bore 336 adapted to receive the intraluminal prosthesis 124. Though the tube is described herein as being "mesh", any suitably stretchable and/or flexible tube such as a cloth/elastic tube, an intraluminal prosthesis, or any other suitable means could be used. A mesh, when used, may be made of any of various materials, such as polyethylene napthalate (PEN), polytetrafluoroethylene (PTFE), expanded PTFE, polyurethane, Vectran, polypropelene, or any other suitable material. The mesh could also have any of a variety of different profiles, braiding or weaving patterns as desired. For example, 96 strand 3 mil round Nylon monofilaments may be braided in an under-2, over-2 pattern with 16 pic. The mesh may be chosen to have density, strength, or other properties sufficient to keep portions of the intraluminal prosthesis 124 from poking through, ripping, scoring, or otherwise damaging the mesh tube 330.

The apparatus 328 includes a first attachment block 338 and a second attachment block 340. The first and second attachment blocks 338 and 340 are each adapted to grasp one of the first and second tube ends 332 and 334 in any suitable manner. For example, and as shown in the Figures, the first and second attachment blocks 338 and 340 may have a selectively openable split structure, with a gripping surface, such as the depicted serrations, helping retain the first and second tube ends 332 and 334. Alternately, and not shown in the Figures, a cross-hatched or friction-coated surface could help retain the first and second tube ends 332 and 334, each tube end 332 or 334 could be fastened to a bolt or clip protruding from an attachment block 338 or 340 having a one-piece structure, or any other retention means could secure the tube ends 332 or 334 to the attachment blocks 338 or 340.

A block frame 342 connects the first and second attachment blocks 338 and 340 for relative longitudinal movement therebetween. For instance, and as shown by the arrow 344 in FIG. 3, the second attachment block 340 may be held stationary while a telescoping arm 346 pulls the first attachment block 338 away from the second attachment block. Alternately, a bi-directional powered mechanism could move both the first and second attachment blocks 338 and 340 at substantially the same time or in a predetermined sequence. The block frame 342 may be of any suitable configuration and may be actively or passively powered in any suitable manner to produce the desired relative motion between the first and second attachment blocks 338 and 340.

A sequence of operation of the apparatus 328 is shown in the partial perspective views of FIGS. 4 and 5. The apparatus 328 may be used to compress any suitable intraluminal prosthesis 124, with or without another structure, such as a catheter balloon (not shown) located inside the compressed intraluminal prosthesis. This description, however, will presume that the apparatus 328 is being used to compress an intraluminal prosthesis 124 for use in the intraluminal prosthesis cartridge 100 of FIGS. 1 and 2. The intraluminal prosthesis 124 may be a lined intraluminal prosthesis, having a layer of synthetic or biological material covering at least part of an inner or outer surface of the intraluminal prosthesis, or may be an unlined intraluminal prosthesis, as shown in FIGS. 3-5 for clarity.

The intraluminal prosthesis 124 is placed completely within the mesh tube 330 preparatory to compression of the intraluminal prosthesis. Additionally, any structures about which the intraluminal prosthesis 124 is to be compressed, such as the catheter balloon, should be located inside or passed through the intraluminal prosthesis before compression. For instance, and as shown in FIG. 4, the cartridge inner sheath 104, with attached nose cone 110, is placed within and extends through the uncompressed intraluminal prosthesis 124. The stopper 120 may also be placed within the uncompressed intraluminal prosthesis 124 or within the mesh tube 330. Depending upon the application of the apparatus 328, such included structures may be wholly contained within the mesh tube 330 during intraluminal prosthesis 124 compression or may protrude (not shown) from the first or second tube end 332 or 334.

After the intraluminal prosthesis 124 and any structures therein have been arranged as desired within the relaxed or untensioned mesh tube 330, the first attachment block 338 is removably attached to the first tube end 332 and the second attachment block 340 is removably attached to the second tube end 334. It is desirable for the first and second attachment blocks 338 and 340 to grasp the mesh tube 330 at locations at least slightly spaced apart longitudinally from the intraluminal prosthesis 124 to avoid applying unwanted forces to the intraluminal prosthesis 124.

Once engaged with the first and second attachment blocks 338 and 340, the mesh tube 330 is stretched in a longitudinal dimension through relative motion of the first and second attachment blocks 338 and 340. That is, the block frame 342 moves at least one of the first and second attachment blocks 338 and 340 to separate the attachment blocks longitudinally. The relative movement between the first and second attachment blocks 338 and 340 applies a tensile force 450 to stretch the mesh tube 330 longitudinally, which in turn causes the mesh tube to reduce size or constrict in a radial direction and thereby radially compress the intraluminal prosthesis 124 to a reduced diameter condition. The uniform radial force exerted by the mesh tube 330 on the intraluminal prosthesis 124 is shown by the compression arrows 552 in FIG. 5. This phenomenon is similar to that operative in popular woven-straw "finger trap" toys.

The mesh tube 330 may be stretched as much as needed to achieve a desired compression of the intraluminal prosthesis 124 and the material of the mesh tube 330 should be chosen to have strength and deformation properties accordingly. For example, the mesh tube 330 may be designed to minimize stretching in a longitudinal direction while maximizing inward radial force exerted by the tube 330. When the intraluminal prosthesis 124 is a lined intraluminal prosthesis, the greater compression forces needed may necessitate a stronger or more rigid mesh tube 330 than for an unlined intraluminal prosthesis. The mesh tube 330 may be designed to accommodate some degree of local deformation which may help prevent friction or puncture damage to the lining, when present, by other structures of the intraluminal prosthesis 124. However, it may be desirable to minimize overall deformation or stretching of the mesh tube 330.

A crescent-, ring-, or donut-shaped assistance structure (not shown) is optionally provided to assist with compression of the intraluminal prosthesis 124 and provide an inward radial force in addition to that exerted by the mesh tube 330. Before or after the mesh tube 330 is stretched by the first and second attachment blocks 338 and 340, the assistance structure may be placed around at least a portion of the mesh tube 330 and be moved along the mesh tube 330 to further squeeze and compress the intraluminal prosthesis 124.

A longitudinal measuring gage 347 or other measuring device, shown schematically in FIG. 3, may indicate the amount of relative longitudinal movement between the first and second attachment blocks 338 and 340. The gage 347 may additionally or instead indicate the amount of longitudinal force developed between the first and second attachment blocks 338 and 340. The gage 347 may be of any suitable type, such as, but not limited to, a dial, a linear scale, a ratchet wheel, an audible or visual binary limit switch or any other indicator type. The gage 347, when present and when used with a suitably selected mesh tube 330, assists the operator in applying a precise amount of radial compressive force to the intraluminal prosthesis 124. Therefore, overcompression or undercompression of the intraluminal prosthesis 124 can be avoided. Optionally, the gage 347 could interface with a power source for the first and/or second attachment blocks 338 and 340 to slow or halt relative movement of the attachment blocks when a certain longitudinal relative movement amount and/or longitudinal force has been achieved. The gage 347 may be calibrated in any suitable manner and at any desired time, such as at a predetermined interval of time. The gage 347 should be calibrated each time a different type, size, structure, or material of mesh tube 330 is used.

Optionally, and as shown in FIG. 3, a liquid bath 348 may be provided to help express any air contained within the intraluminal prosthesis. Since air bubbles introduced into the patient's body by the intraluminal prosthesis 124 may cause embolisms or other unwanted consequences, the liquid bath 348 may be desirable to facilitate the compression of the intraluminal prosthesis 124 without trapping air within the folds of the intraluminal prosthesis. The liquid may be a chemically inert liquid, such as glycerine or saline, and/or may be used to help maintain a sterile environment around the intraluminal prosthesis 124. The liquid may contain a therapeutic agent which the intraluminal prosthesis 124 or another structure of the stent cartridge 100 can absorb or store for later release. The liquid bath may hydrate and/or lubricate the intraluminal prosthesis 124, particularly a lined intraluminal prosthesis, to avoid damage to the intraluminal prosthesis or lining during the compression process. When a liquid bath 348 is used, the intraluminal prosthesis 124 is submerged in the liquid bath, the intraluminal prosthesis 124 is compressed while submerged, and then the airless compressed intraluminal prosthesis 124 is removed from the liquid bath. The intraluminal prosthesis cartridge 100 may be designed to capture and contain a quantity of the liquid from the liquid bath sufficient to help keep the intraluminal prosthesis 124 hydrated and sterile during storage. Alternately, the intraluminal prosthesis cartridge 100 could include a fitting or other structure (not shown) allowing for fluids to be added to or removed from within the intraluminal prosthesis cartridge 100 at a later time.

To construct the intraluminal prosthesis cartridge 100 as shown in FIGS. 1 and 2, the intraluminal prosthesis 124 needs to be placed within the intraluminal prosthesis sheath 112 and maintained therein in a compressed condition after the compression process. The intraluminal prosthesis sheath 112 confines the compressed intraluminal prosthesis 124 adequately, but must be placed around the intraluminal prosthesis 124 before the stretched mesh tube 330 is removed from the compressed intraluminal prosthesis 124 so that the intraluminal prosthesis 124 does not "relax" and decompress. This relaxation is possible even with an intraluminal prosthesis 124 which is not self-expanding, if the intraluminal prosthesis 124 has been compressed beyond a normal resting compression.

To position the intraluminal prosthesis sheath 112 around the intraluminal prosthesis 124, at least a portion of the mesh tube 330 is placed within the intraluminal prosthesis sheath, optionally before the intraluminal prosthesis is compressed. This relationship of position between the intraluminal prosthesis sheath 112 and the mesh tube 330 is highly dependent upon the particular configuration of the first and second attachment blocks 338 and 340 and is shown merely schematically in FIG. 5. The longitudinal dimension and configuration of the mesh tube 330 may be chosen to facilitate the desired relationship between the intraluminal prosthesis sheath 112 and the mesh tube. For example, the mesh tube 330 could be slightly longer than the total combined lengths of the intraluminal prosthesis 124 and the intraluminal prosthesis sheath 112, with the intraluminal prosthesis 124 placed within the mesh tube near one of the first and second tube ends 332 and 334 and the intraluminal prosthesis sheath 112 placed around the mesh tube near the other of the first and second tube ends. In such a configuration, both the intraluminal prosthesis 124 and the intraluminal prosthesis sheath 112 would be located between the first and second tube ends 332 and 334. Alternately, the first or second attachment block 338 or 340 could include a mechanism (not shown) to allow the intraluminal prosthesis sheath 112 to feed therethrough to surround the mesh tube 330 before or after compression, and a suitable arrangement for such positioning could readily be provided by one of ordinary skill in the art.

Once the intraluminal prosthesis has been compressed, the intraluminal prosthesis sheath 112 is slid along the mesh tube 330 until the compressed intraluminal prosthesis (still contained within the mesh tube) is positioned as desired within the intraluminal prosthesis sheath bore 118. At this time, the stopper 120 and nose cone 110 should be positioned relative to the intraluminal prosthesis sheath 112 as needed to complete formation of the annular intraluminal prosthesis space 122 with the intraluminal prosthesis 124 and a portion of the mesh tube 330 contained therein.

The mesh tube 330 must then be removed from the intraluminal prosthesis sheath 112. First, tension is removed from the mesh tube 330 by relative longitudinal movement of the first and second attachment blocks 338 and 340 closer together. At least one of the first and second attachment blocks 338 and 340 is removed from the mesh tube 330. Optionally, the tails of the mesh tube 330 protruding from the intraluminal prosthesis sheath 112 are trimmed. For example, approximately one-eighth inch of mesh may be left adjacent the nose cone 110 and approximately one-quarter inch may be left adjacent the stopper 120.

The mesh tube 330 may be removed from the intraluminal prosthesis sheath 112 using any of a variety of methods. For example, the mesh could be dismantled and pulled from the intraluminal prosthesis sheath 112 a single strand or a few strands at a time. As another example, a stretchable tube with a ripcord seam or bridgestone strand (not shown) could be used as a mesh tube 330, and the entire tube could be removed at once after the ripcord is removed to lay open the tube structure. As yet another example, the mesh tube 330 could simply be pulled from the intraluminal prosthesis sheath 112 without any disassembly. Note that either the stopper 120 or the nose cone 110 helps resist the pulling motion and keep the intraluminal prosthesis 124 in place within the annular intraluminal prosthesis space 122 during removal of the mesh, depending upon the direction from which the mesh tube 330 components are being pulled.

It is contemplated that at least one of the stopper 120 and nose cone 110 may fit slightly loosely within the intraluminal prosthesis sheath bore 118 to allow for easier removal of the mesh tube 330. If such is the case, the stopper 120 and/or nose cone 110 may be tightened within the intraluminal prosthesis sheath bore 118 once the mesh tube 330 is removed. A longitudinally tapered structure (not shown) of the stopper 120 and/or nose cone 110 may facilitate this tightening process.

While aspects of the present invention have been particularly shown and described with reference to the preferred embodiment above, it will be understood by those of ordinary skill in the art that various additional embodiments may be contemplated without departing from the spirit and scope of the present invention. For example, one of the first or second attachment blocks 338 and 340 may be permanently attached to the mesh tube 330 and optionally assists in removing the mesh tube 330 from the intraluminal prosthesis sheath 112. The liquid bath 348 could be used to impregnate or saturate the intraluminal prosthesis 124 or a related structure with a therapeutic or preservative substance, optionally through pressurizing the liquid bath. An "airless" intraluminal prosthesis 124 may still include a very small amount of trapped air. A storage bracket could hold the first and second tube ends 332 and 334 to maintain the mesh tube 330 in a tensioned position and thereby store the compressed intraluminal prosthesis 124 for later use. When the compression is achieved using a liquid bath, some of the liquid may remain within the intraluminal prosthesis sheath 112 and help provide hydration and/or a sterile storage means for the intraluminal prosthesis 124. The mesh tube 330 could be dissolvable or otherwise self-degradable, either during storage/transportation of the assembled intraluminal prosthesis cartridge 100 or during/after the intraluminal prosthesis 124 is installed in the patient. The stopper 120 or nose cone 110 may be installed in the intraluminal prosthesis cartridge 100 after the intraluminal prosthesis sheath 112 surrounds the intraluminal prosthesis 124. The stopper 120 or any other structure may be colored or patterned to enhance visibility of that structure through the mesh tube 330 or another covering. A device or method incorporating any of these features should be understood to fall under the scope of the present invention as determined based upon the claims below and any equivalents thereof.

The method and apparatus of certain embodiments of the present invention, when compared with other apparatus and methods, may have the advantages of economically and efficiently providing even compression pressure, allowing for ease in transporting and storing a compressed intraluminal prosthesis, and avoiding mechanical or dehydration damage to a lined intraluminal prosthesis.

Other aspects, objects, and advantages of the present invention can be obtained from a study of the drawings, the disclosure, and the appended claims.

Having described the invention, the following is claimed:

1. A method for compressing an intraluminal prosthesis, the method comprising the steps of:
   providing a mesh tube having first and second longitudinally spaced tube ends and a hollow tube bore located therebetween;
   inserting the intraluminal prosthesis completely into the hollow tube bore;
   stretching the tube in a longitudinal dimension, which reduces the tube in a radial dimension and causes the intraluminal prosthesis to radially compress, including the steps of:
      grasping the first and second tube ends at locations spaced apart longitudinally from the intraluminal prosthesis;
      applying tensile force to at least one of the first and second tube ends; and
      relatively moving the first and second ends longitudinally apart.

2. The method of claim 1, further including the steps of:
   submerging the intraluminal prosthesis and at least a portion of the tube in a liquid bath before compressing the intraluminal prosthesis; and
   removing the intraluminal prosthesis from the liquid bath after compression.

3. The method of claim 1, further including the steps of:
   measuring the longitudinal stretching of the tube with a measuring instrument; and
   calibrating the measuring instrument at a predetermined interval of time.

\* \* \* \* \*